US010195253B2

(12) United States Patent
Schwager

(10) Patent No.: US 10,195,253 B2
(45) Date of Patent: Feb. 5, 2019

(54) IMMUNOCYTOKINE COMBINATION THERAPY

(75) Inventor: Kathrin Schwager, Zurich (CH)

(73) Assignee: PHILOGEN S.P.A., Siena (IT)

( * ) Notice: Subject to any disclaimer, the term of this patent is extended or adjusted under 35 U.S.C. 154(b) by 101 days.

(21) Appl. No.: 14/346,997

(22) PCT Filed: Jun. 29, 2012

(86) PCT No.: PCT/EP2012/062705

§ 371 (c)(1),
(2), (4) Date: Mar. 25, 2014

(87) PCT Pub. No.: WO2013/045125

PCT Pub. Date: Apr. 4, 2013

(65) Prior Publication Data

US 2014/0219920 A1    Aug. 7, 2014

Related U.S. Application Data

(60) Provisional application No. 61/539,131, filed on Sep. 26, 2011.

(51) Int. Cl.
| | | |
|---|---|---|
| *A61K 38/00* | (2006.01) | |
| *A61K 38/19* | (2006.01) | |
| *A61K 38/20* | (2006.01) | |
| *A61K 47/68* | (2017.01) | |
| *A61K 49/00* | (2006.01) | |
| *C07K 14/55* | (2006.01) | |
| *C07K 16/18* | (2006.01) | |
| *C07K 14/525* | (2006.01) | |

(52) U.S. Cl.
CPC ........ *A61K 38/191* (2013.01); *A61K 38/2013* (2013.01); *A61K 47/6813* (2017.08); *A61K 47/6843* (2017.08); *A61K 47/6851* (2017.08); *A61K 49/00* (2013.01); *C07K 14/525* (2013.01); *C07K 14/55* (2013.01); *C07K 16/18* (2013.01); *A61K 38/00* (2013.01); *C07K 2317/622* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 8,623,373 B2 | 1/2014 | Zardi et al. | |
| 2004/0013640 A1 | 1/2004 | Zardi et al. | |
| 2010/0316602 A1 | 12/2010 | Zardi et al. | |
| 2011/0064751 A1* | 3/2011 | Mossner et al. | 424/178.1 |
| 2011/0300186 A1* | 12/2011 | Hellstrom et al. | 424/400 |

FOREIGN PATENT DOCUMENTS

WO         01/62298 A2    8/2001

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Vajdos et al. (J Mol Biol. Jul. 5, 2002;320(2):415-28 at 416).*
Brown et al. (J Immunol. May 1996;156(9):3285-91.*
Gayvert (PLoS Comput Biol. Jan. 13, 2017;13(1):e1005308) (Year: 2017).*
Yin et al (Front Pharmacol. 2018; 9: 535) (Year: 2018).*
Tallarida et al. (Pharmacol. Ther. 2010; 127, 165-174) (Year: 2010).*
International Search Report dated Oct. 4, 2012 issued in corresponding PCT/EP2012/062705 application (pp. 1-5).
C. Halin et al., "Synergistic Therapeutic Effects of a Tumor Targeting Antibody Fragment, Fused to Interleukin 12 and to Tumor Necrosis Factor Alpha", Cancer Research, vol. 63, No. 12 (Jun. 15, 2003) pp. 3202-3210.
B. Carnemolla et al., "Enhancement of the Antitumor Properties of Interleukin-2 by its Targeted Delivery to the Tumor Blood Vessel Extracellular Matrix", Blood, American Society of Hematology, vol. 99, No. 5 (Mar. 1, 2002) pp. 1659-1665.
O. Christ et al., "Interleukin 2-Antibody and Tumor Necrosis Factor-Antibody Fusion Proteins Induce Different Antitumor Immune Responses in Vivo", Clinical Cancer Research, vol. 7, No. 5 (May 1, 2001) pp. 1385-1397.
E. Balza et al., "Therapy-Induced Antitumor Vaccination in Neuroblastomas by the Combined Targeting of IL-2 and TNF[alpha]", International Journal of Cancer, vol. 127, No. 1 (Jul. 1, 2010) pp. 101-110.
L. Borsi et al., "Selective Targeted Delivery of TNF to Tumor Blood Vessels", Blood, vol. 102, No. 13 (Dec. 15, 2003) pp. 4384-4392.
K. Schwager et al., "The Immunocytokine L19-IL2 Eradicates Cancer When Used in Combination with CTLA-4 Blockade or with L19-TNF", Journal of Investigative Dermatology, vol. 00 (2012) pp. 1-9.
International Preliminary Report on Patentability dated Apr. 1, 2014 issued in corresponding PCT/EP2012/062705 application (pp. 1-5).
R.A. Maas et al., "Intratumoral Low-Dose Interleukin-2 Induces Rejection of Distant Solid Tumour", Cancer Immunology Immunotherapy., vol. 33 (1991) pp. 389-394.
A.S. Pak et al., "Treating Tumor-Bearing Mice with Low-Dose g-Interferon plus Tumor Necrosis Factor alpha to Diminish Immune Suppressive Granulocyte-Macrophage Progenitor Cells Increases Responsiveness to Interleukin 2 Immunotherapy", Cancer Research, vol. 55 (Feb. 15, 1995) pp. 885-890.

(Continued)

*Primary Examiner* — Brian Gangle
*Assistant Examiner* — Andrea K McCollum
(74) *Attorney, Agent, or Firm* — Millen, White, Zelano & Branigan, PC

(57) ABSTRACT

Methods and compositions for treating tumors, especially skin tumors, by locally administering single doses of tumor necrosis factor alpha (TNFα) and interleukin-2 (IL2) at the tumor site, where the TNFα and IL2 are delivered as immunoconjugates comprising an antibody targeted to a splice isoform of an extracellular matrix component such as fibronectin.

17 Claims, 4 Drawing Sheets

Specification includes a Sequence Listing.

(56) References Cited

OTHER PUBLICATIONS

O. Christ et al., "Efficacy of Local versus Systematic Application of Antibody-Cytokine Fusion Proteins in Tumor Therapy", Clinical Cancer Research, vol. 7 (Apr. 2001) pp. 985-998.

M.S. Sabel et al., "Synergistic Effect of Intratumoral IL-12 and TNF-alpha Microspheres: Systematic Anti-Tumor Immunity is Mediated by Both CD8+ CTL and NK Cells", Surgery, vol. 142, No. 5 (Nov. 2007) pp. 749-760.

M.S. Sabel et al., "Intratumoral Delivery of Encapsulated IL-12, IL-18 and TNF-alpha in a Model of Metastatic Breast Cancer", Breast Cancer Research Treatment, vol. 122 (2010) pp. 325-336.

B. Weide et al., "High Response Rate After Intratumoral Treatment With Interleukin-2", Cancer (Sep. 1, 2010) pp. 4139-4146.

T. Nishimura et al., "Combination Tumor-Immunotherapy With Recombinant Tumor Necrosis Factor and Recombinant Interleukin 2 in Mice", International Journal of Cancer, vol. 40 (1987) pp. 255-261.

Y. Nio et al., "In Vivo Effects of Human Recombinant Tumor Necrosis Factor Alone and in Combination with other Biological Response Modifiers on Human Digestive Organ Cancer Xenografts Transplanted in Nude Mice", Biotherapy, vol. 3 (1991) pp. 337-344.

E.E. Johnson et al., "Intratumoral Immunocytokine Treatment Results in Enhanced Antitumor Effects", Cancer Immunology Immunotherapy, vol. 57, No. 12 (Dec. 2008) pp. 1891-1902.

A. Ribas et al., "Phase I/II Open-Label Study of the Biologic Effects of the Interleukin-2 Immunocytokine EMD 273063 (hu I 4.I 8-IL2) in Patients with Metastatic Malignant Melanoma", Journal of Translational Medicine, vol. 7, No. 68 (Jul. 29, 2009) pp. 1-11.

T.L. Whiteside et al., "Evidence for Local and Systemic Activation of Immune Cells by Peritumoral Injections of Interleukin 2 in Patients with Advanced Squamous Cell Carcinoma of the Head and Neck", Cancer Research, vol. 53 (Dec. 1, 1993) pp. 5654-5662.

Danielli, R., et al., "Intralesional administration of L19-IL2/L19-TNF in stage III or stage IVM1a melanoma patients: results of a phase II study," Cancer Immunol Immunother, DOI 10.1007/s00262-015-1704-6, Published online: May 15, 2015—11 pages.

* cited by examiner

VH

EVQLLESGGGLVQPGGSLRLSCAASGFTFSSFSMSMSWVRQAPGKGLEWVSSISGSSGTTYYADSVKGRFT
                                    CDR1                             CDR2

ISRDNSKNTLYLQMNSLRAEDTAVYYCAKPFPYFDYWGQGTLVTVSS
                           CDR3

LINKER

GDGSSGGSGGAS

VL

EIVLTQSPGTLSLSPGERATLSCRASQSVSSSFLAWYQQKPGQAPRLLIYYASSRATGIPDRFSGS
                                 CDR1                                CDR2

GSGTDFTLTISRLEPEDFAVYYCQQTGRIPPTFGQGTKVEIK
                            CDR3

Fig. 3

SEQUENCE LISTING

<160> NUMBER OF SEQ ID NOS: 10

<210> SEQ ID NO 1
<211> LENGTH: 5
<212> TYPE: PRT
<213> ORGANISM: Homo sapiens

<400> SEQUENCE: 1

Ser Phe Ser Met Ser
1               5

<210> SEQ ID NO 2
<211> LENGTH: 17
<212> TYPE: PRT
<213> ORGANISM: Homo sapiens

<400> SEQUENCE: 2

Ser Ile Ser Gly Ser Ser Gly Thr Thr Tyr Tyr Ala Asp Ser Val Lys
1               5                   10                  15

Gly

<210> SEQ ID NO 3
<211> LENGTH: 7
<212> TYPE: PRT
<213> ORGANISM: Homo sapiens

<400> SEQUENCE: 3

Pro Phe Pro Tyr Phe Asp Tyr
1               5

<210> SEQ ID NO 4
<211> LENGTH: 12
<212> TYPE: PRT
<213> ORGANISM: Homo sapiens

<400> SEQUENCE: 4

Arg Ala Ser Gln Ser Val Ser Ser Ser Phe Leu Ala
1               5                   10

<210> SEQ ID NO 5
<211> LENGTH: 7
<212> TYPE: PRT
<213> ORGANISM: Homo sapiens

```
<400> SEQUENCE: 5

Tyr Ala Ser Ser Arg Ala Thr
1               5

<210> SEQ ID NO 6
<211> LENGTH: 9
<212> TYPE: PRT
<213> ORGANISM: Homo sapiens

<400> SEQUENCE: 6

Gln Gln Thr Gly Arg Ile Pro Pro Thr
1               5

<210> SEQ ID NO 7
<211> LENGTH: 116
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Gly Thr Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 8
<211> LENGTH: 12
<212> TYPE: PRT
<213> ORGANISM: Artificial sequence
<220> FEATURE:
<223> OTHER INFORMATION: Synthetic sequence: Peptide linker

<400> SEQUENCE: 8

Gly Asp Gly Ser Ser Gly Gly Ser Gly Gly Ala Ser
1               5                   10

<210> SEQ ID NO 9
<211> LENGTH: 108
<212> TYPE: PRT
<213> ORGANISM: Homo sapiens

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45
```

-continued

```
Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Gly Arg Ile Pro
                 85                  90                  95

Pro Thr Phe Gly Gln Gly Thr Lys Val Glu Ile Lys
            100                 105

<210> SEQ ID NO 10
<211> LENGTH: 236
<212> TYPE: PRT
<213> ORGANISM: Artificial sequence
<220> FEATURE:
<223> OTHER INFORMATION: Synthetic sequence: scFv-L19

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
             20                  25                  30

Ser Met Ser Trp Val Arg Gln Ala Pro Gly Lys Gly Leu Glu Trp Val
             35                  40                  45

Ser Ser Ile Ser Gly Ser Ser Gly Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
        130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235
```

IMMUNOCYTOKINE COMBINATION THERAPY

FIELD OF THE INVENTION

This invention relates to combination therapy for tumours in which a TNFα immunoconjugate and an IL2 immunoconjugate are administered directly to the tumour site.

BACKGROUND

Tumour necrosis factor alpha (TNFα) is a cytokine produced by many cell types, mainly activated monocytes and macrophages. It is expressed as a 26 kDa integral transmembrane precursor protein from which a mature protein of approximately 17 kDa is released by proteolytic cleavage. The soluble bioactive TNFα is a homotrimer that binds cell surface receptors. TNFα has been shown to induce necrosis of solid tumours. It exerts its effects mainly on the endothelium of the tumour-associated vasculature, with increased permeability, upregulation of tissue factor, fibrin deposition and thrombosis, and massive destruction of the endothelial cells.

Interleukin-2 (IL2), a four a helix bundle cytokine produced by T helper 1 cells, plays an essential role in the activation phases of both adaptive and innate immune responses. Although it is not believed to have a direct cytotoxic effect on cancer cells, it has been reported to induce tumour regression by stimulating a cell-mediated immune response.

Intratumoural injections of IL2 have been trialled in metastatic melanoma patients [1]. In that study, treatment was administered three times weekly for at least 2 weeks, and overall 69% of patients were reported to achieve a complete response.

WO01/66298 described immunoconjugates comprising TNFα and IL2 respectively, fused to antibody L19. L19 specifically binds the ED-B domain of fibronectin isoform B-FN, which is one of the best known markers angiogenesis (U.S. Ser. No. 10/382,107; WO01/62298). ED-B is an extra domain of 91 amino acids found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

Carnemolla et al. [2] described enhancement of the anti-tumour properties of IL2 by its targeted delivery to the tumour blood vessel extracellular matrix in an L19-IL2 immunoconjugate.

Christ et al. [3] described intratumoural administration of an IL2 immunoconjugate, a TNFα immunoconjugate, or antibody alone. The antibody used was anti-EGFR, which had an anti-tumour effect. An anti-tumour immune response was reported following multiple injections of either fusion protein.

Borsi et al. [4] reported a study in which L19-TNFα and L19-IL2 immunoconjugates were administered intravenously to mice on days 7 and 10 following implantation of tumour cells. L19 was used to concentrate and maximise the anti-tumour effects of the systemically delivered cytokines. The combination of immunocytokines was reported to have a synergistic effect on tumour volume. Mice who received the combination treatment had markedly reduced tumour volume compared with those who received just one immunocytokine.

SUMMARY OF THE INVENTION

Reported here are unexpected effects on tumours resulting from local administration of a combination of immunocytokines, TNFα-L19 and IL2-L19, at the tumour site. A single administration of these two immunocytokines promoted the complete eradication of large subcutaneous tumours in mice.

Mice received a single intratumoural injection of the TNFα-L19, a single intratumoural injection of IL2-L19, or the combination. No further treatments were given. Tumour volume was measured daily and it was observed that tumours in mice treated with the combination therapy rapidly reduced in size and appeared to be completely eliminated within a period of days and showed no regrowth. Compared with saline-treated control mice, mice treated with one cytokine alone also showed inhibition of tumour growth, but tumours in these mice nevertheless continued to increase slowly in size. These results show a synergistic effect of the combined cytokine therapy, and a remarkable therapeutic effect, in which tumours were eradicated following just a single dose of each cytokine.

Accordingly, a first aspect of the invention is a method of treating a tumour in a patient by injecting a single dose of a TNFα immunoconjugate and a single dose of an IL2 immunoconjugate at the tumour site.

The immunoconjugate comprises the cytokine linked to an antibody molecule, which targets the cytokine to the site of the lesion. The antibody molecule binds a splice isoform of an extracellular matrix component, which is selectively expressed by the extracellular matrix in tumour tissue. By combining this targeting effect with direct administration of the immunoconjugate to the tumour site, a very localised administration is achieved, which concentrates the effect of the cytokines at the tumour site and reduces side effects and toxicity associated with systemic use of the cytokines.

A number of splice isoforms of tumour extracellular matrix components are known, and antibody molecules targeting any such isoform may be used to selectively target the tumour. These include splice isoforms of fibronectin, such as B-FN. B-FN includes an extra domain ED-B, and antibody molecules of the invention are preferably targeted to this domain. A preferred antibody molecule comprises the complementarity determining regions (CDRs) of antibody L19. These are, as illustrated in FIG. 3:

| VH CDR1 | SFSMS | SEQ ID NO: 1 |
| VH CDR 2 | SISGSSGTTYYADSVKG | SEQ ID NO: 2 |
| VH CDR 3 | PFPYFDY | SEQ ID NO: 3 |
| VL CDR 1 | RASQSVSSSFLA | SEQ ID NO: 4 |
| VL CDR 2 | YASSRAT | SEQ ID NO: 5 |
| VL CDR 3 | QQTGRIPPT | SEQ ID NO: 6 |

The TNFα immunoconjugate preferably comprises TNFα linked to an antibody molecule. comprising the L19 CDRs. The IL2 immunoconjugate comprises IL2 linked to an antibody molecule, which may be an identical or different antibody molecule as the TNFα immunoconjugate. The antibody molecule in each immunoconjugate may bind the same extracellular matrix component, optionally the same splice isoform e.g. they may bind the same domain. Preferably, the IL2 immunoconjugate comprises IL2 linked to an antibody molecule comprising the L19 CDRs.

Preferably, the antibody molecule (of the TNFα and/or the IL2 immunoconjugate) comprises the L19 VH domain and/or the L19 VL domain. Amino acid sequences of the L19 VH and VL domains are SEQ ID NO: 7 and SEQ ID NO: 9 respectively (FIG. 3).

Preferably the antibody molecule is a single chain Fv (scFv) or other antibody fragment of low molecular weight and/or lacking an Fc region. These properties assist with targeting and tissue penetration of the immunoconjugate at the tumour site. A preferred antibody molecule is scFv-L19, which is an scFv comprising an L19 VH domain and an L19 VL domain, wherein the VH and VL are conjoined in a single polypeptide chain by a peptide linker sequence. The VH domain contains VH CDR1, CDR2 and CDR3 sequences, and the VL domain contains VL CDR1, CDR2 and CDR3 sequences. The VH domain may have an amino acid sequence as set out in FIG. 3 (SEQ ID NO: 7). The VL domain may have an amino acid sequence as set out in FIG. 3 (SEQ ID NO: 9). The VH and VL domains are normally joined by a peptide linker such as the 12 residue linker shown in FIG. 3 (SEQ ID NO: 8). Preferably, the scFv-L19 comprises or consists of the amino acid sequence shown in FIG. 3 (SEQ ID NO: 10).

A molecular linker such as a peptide may be used to join the cytokine to the antibody molecule, facilitating expression of all or part of the immunocytokine as a fusion protein. Where the antibody molecule is also a single chain molecule, such as scFv, the entire immunocytokine polypeptide chain may conveniently be produced as a fusion protein. For the TNFα immunoconjugate, the fusion proteins are then assembled into trimers, allowing TNFα to adopt its normal trimeric form [4].

Optionally, the immunocytokine carries a detectable and/or functional label, such as a radioactive isotope. Radiolabelled L19, and its use in cancer therapy, has been described before.

It is generally convenient to provide the IL2 immunoconjugate and the TNFα immunoconjugate as separate molecules. They may be provided as a combined preparation, or as separate formulations to permit either simultaneous or sequential administration. The clinician can determine the most suitable manner of administering the single dose of each immunocytokine to the patient. For example, the method of treatment may comprise injecting the TNFα immunoconjugate and the IL2 immunoconjugate in separate injections, simultaneously or sequentially. Where sequential administration is used, the immunocytokines are preferably injected within 24 hours, 12 hours, 1 hour or more preferably within 30 minutes of each other. The two immunocytokines may be injected at the same point in the tumour site, or at different points. A combined injection of both immunocytokines may be administered. It may be preferable to administer a dose in multiple injections, for example to inject multiple locations across the tumour or around the tumour site, or to facilitate administration of a larger volume of immunocytokine.

The dose is an amount of cytokine, administered at one time, effective to treat the tumour in the combination therapy according to the invention. A single dose may be administered in a treatment period of 1 hour or less, preferably in a period of 30 minutes or less, e.g. 15, 10, 5 or 1 minute or less.

The quantity of TNFα or IL2 administered will depend on the size and nature of the tumour, among other factors. For example, the dose of an TNFα-scFv immunoconjugate may be in the range of 2-20 μg, e.g. 5-10 μg. The dose of IL2-scFv immunoconjugate may be in the range of 10-100 μg, e.g. 20-40 μg. Corresponding doses using other immunoconjugate formats may be straightforwardly calculated to administer an appropriate quantity of cytokine. These are examples only and, of course, different doses may be used. The clinician will determine a therapeutically effective amount for administration.

As reported here, a single dose of the TNFα immunoconjugate and a single dose of the IL2 immunoconjugate were sufficient for tumour therapy. Multiple doses were not required, and treatment of a tumour according to the present invention does not comprise repeating the combination therapy. In addition to the advantages this offers to patients, the single dose regimen provides a considerable advantage to clinicians and significant cost savings.

Accordingly, in treating a particular tumour, the method of the invention is not repeated. The method of treating the tumour may comprise:

(a) injecting a single dose of the TNFα immunoconjugate and a single dose of the IL2 immunoconjugate at the tumour site, and not repeating step (a).

The tumour is treated without any repeated administration of the combination of immunocytokines to the tumour site. As shown herein, a tumour may be treated without any subsequent injection of a TNFα immunoconjugate or an IL2 immunoconjugate. Indeed, the tumour may be treated without administering any further anti-cancer agent to the patient. Optionally, the patient has not previously been given either TNFα or IL2 for the tumour, although in some cases a patient may have received previous therapy with only one of IL2, TNFα or an immunoconjugate including one of these cytokines, which did not achieve complete treatment of the tumour.

Accordingly, a method of the invention may comprise treating a tumour in a patient by injecting a dose of the TNFα immunoconjugate and a dose of the IL2 immunoconjugate at the tumour site, wherein the tumour is treated without administering any subsequent dose of the TNFα immunoconjugate or the IL2 immunoconjugate to the tumour site.

Of course, the method of the invention may be used to treat multiple tumours in a patient, by performing the method on each tumour.

Other treatments that may be used in combination with the invention include the administration of suitable doses of pain relief drugs such as non-steroidal anti-inflammatory drugs (e.g. aspirin, paracetamol, ibuprofen or ketoprofen) or opiates such as morphine, or anti-emetics.

The immunocytokines are injected at the site of the tumour, preferably by intratumoural injection. Peritumoural injection, e.g. local intradermal injection, is another suitable method for administering the immunocytokine locally to a tumour site.

The treated tumour may be a primary tumour or a metastatic tumour. The invention is particularly suited to treatment of skin tumours, e.g. malignant skin tumour, melanoma or carcinoma, since their location is amenable to direct local injection. Other tumours within the body may also be treated, and injections may be guided to tumours within soft tissue or internal organs, e.g. by sonography W. The methods of the invention may also be used in a surgical context, where injection is performed before, during or after tumour surgery.

Treatment of a tumour according to the present invention may include complete eradication of the tumour. The disappearance of any evidence of vital tumour after stopping injections represents complete treatment of the tumour. Disappearance of the tumour may be determined when the tumour has no discernable volume or is no longer visible. Treatment may comprise treatment to eradicate the tumour and prevent tumour regrowth.

A method of treating a tumour according to the present invention may comprise injecting a single dose of the TNFα immunoconjugate and a single dose of the IL2 immunoconjugate at the tumour site, and observing disappearance of the tumour. Absence of tumour regrowth may also be observed.

Patients are preferably monitored during a followup period of at least one month, preferably at least six months or at least a year, after administration of the immunocytokine combination therapy. Disappearance of the tumour, and lack of tumour regrowth, may be observed in the followup period.

In the event of tumour recurrence after the followup period, or if other tumours develop, patients may receive a further treatment with immunocytokine combination therapy according to the invention, to remove the further tumour.

For example, a method according to the invention may comprise eradicating a tumour in a patient by injecting a single dose of the TNFα immunoconjugate and a single dose of the IL2 immunoconjugate at the tumour site, wherein the tumour disappears in the absence of further doses of the TNFα immunoconjugate and/or the IL2 immunoconjugate.

Further aspects of the invention relate to TNFα and IL2 immunoconjugates for use in any of the methods of the invention described herein. A composition comprising the TNFα immunoconjugate and/or the IL2 immunoconjugate may be provided for use in a method as described. Compositions may further comprise additional components, such as pharmaceutically acceptable excipients. A composition may comprise the immunocytokines as separate formulations (e.g. separately packaged, optionally in a kit), or as a combined formulation. The formulation may be adapted for intratumoural administration. Use of the TNFα immunoconjugate and/or the IL2 immunoconjugate for the manufacture of a medicament for use in a method as described herein is another aspect of the invention.

Nucleic acid molecules encoding immunoconjugates may be provided. The nucleic acids may be present in host cells. A method of producing the immunoconjugate may comprise by expressing the nucleic acid in cultured host cells, optionally followed by purifying the immunoconjugate from the host cell culture. The IL2 and TNFα immunoconjugates are preferably produced in separate cell cultures. They may then be individually formulated as medicaments for administration as described.

DETAILED DESCRIPTION

Certain aspects of the invention are as set out in the appended claims, which may be combined with any other part of the present disclosure.

An antibody molecule is an immunoglobulin whether natural or partly or wholly synthetically produced. The term also covers any polypeptide or protein comprising an antibody antigen-binding site. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide are therefore included. Cloning and expression of chimeric antibodies is well known (EP0120694, EP0125023).

Further techniques available in the art of antibody engineering have made it possible to isolate human and humanised antibodies. For example, human hybridomas can be made as previously described [5]. Phage display is another established technique [5, WO92/01047]. Transgenic mice in which the mouse antibody genes are inactivated and functionally replaced with human antibody genes while leaving intact other components of the mouse immune system, can be used for isolating human antibodies [6].

Synthetic antibody molecules may be created by expression from genes generated by means of oligonucleotides synthesised and assembled within suitable expression vectors [7, 8].

It has been shown that fragments of a whole antibody can perform the function of binding antigens. Antibody fragments are preferred in conjugates of the invention owing to their small size and minimised interaction with other molecules and receptors (e.g. Fc receptor). Particularly preferred are single chain Fv molecules (scFv), wherein a VH domain and a VL domain are linked by a peptide linker which allows the two domains to associate to form an antigen binding site [9, 10]. scFv may be stabilised by the incorporation of disulphide bridges linking the VH and VL domains [11].

Another small antigen-binding antibody fragment is a dAb (domain antibody), namely the variable region of an antibody heavy or light chain [12]. VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation.

An antigen-binding site is the part of a molecule that specifically binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the antibody carrying the antigen-binding site will be able to bind to the various antigens carrying the epitope.

In immunoconjugates of the invention, the antibody molecule binds an extracellular matrix component which is a marker of tumour growth. The extracellular matrix (ECM) is remodelled during tumour growth, and alternative splice variants of ECM components may be selectively expressed at the site of the lesion.

One example is fibronectin. For example, the B-FN isoform of fibronectin contains an extra domain ED-B. An antibody molecule preferably binds specifically to ED-B of fibronectin isoform B-FN. The antibody molecule may comprise the L19 CDRs. For example, the antibody molecule may be an scFv having a VH domain with an amino acid sequence comprising VH CDR1, VH CDR2 and/or VH CDR3 of L19, and a VL domain with an amino acid sequence comprising VL CDR1, VL CDR2 and/or VL CDR3 of L19. An antibody molecule may comprise a VH domain having an amino acid sequence with at least 60%, 65%, 70%, 75%, 80%, 85%, 90%, 95% or 100% sequence identity with the amino acid sequence of the L19 VH domain as set out in SEQ ID NO: 7, and/or comprises a VL domain having an amino acid sequence with at least 60%, 65%, 70%, 75%, 80%, 85%, 90%, 95% or 100% sequence identity with the amino acid sequence of the L19 VL domain as set out in SEQ ID NO: 9. Preferably the antibody molecule is an scFv(L19) comprising an L19 VH domain (SEQ ID NO: 7) and an L19 VL domain (SEQ ID NO: 9). In a preferred embodiment, the antibody molecule is scFv(L19) having the amino acid sequence SEQ ID NO: 10 (FIG. 3).

Modified forms of the L19 VH and/or VL domain may be employed in immunoconjugates of the invention, for example an antibody molecule may comprise the L19 VH or L19 VL domain in which 1, 2, 3, 4 or 5 amino acid substitutions have been made in a CDR and/or framework region, while retaining specific binding to fibronectin ED-B. Such amino acid substitutions are preferably conservative, e.g. substitution of one hydrophobic residue for another, one polar residue for another, arginine for lysine, glutamic for aspartic acid, or glutamine for asparagine.

Another example is tenascin-C (TnC), which exists in various isoforms generated by alternative splicing. In neoplastic tissues TnC containing additional domains are more widely expressed than in normal tissues, especially isoforms containing domain C (cTN-C) (WO00/63699). Thus, an antibody molecule may bind a splice isoform of tenascin-C, e.g. it may bind domain C.

Nucleic acid molecules encoding the immunoconjugates and parts thereof also form part of the invention. The nucleic acid molecule may be a vector, e.g. a plasmid suitable for expression of the nucleotide sequence. Normally the nucleotide sequence is operably linked to a regulatory element such as a promoter for transcription.

The nucleic acid molecules may be contained in a host cell, which may be a cell co-transfected with the nucleic acid molecules or a daughter of such a cell. Cells, especially eukaryotic cells e.g. HEK and CHO cells, or bacterial cells e.g. *Escherichia coli*, containing the nucleic acid molecules also form part of the invention.

Immunoconjugates of the invention may be produced using recombinant techniques, for example by expressing all or part of the immunoconjugate as a fusion protein. Normally the expression is performed in a host cell containing nucleic acid, as described above. Expression may therefore comprise culturing such a host cell. For TNFα fusion proteins, trimerisation of the subunits may occur in the cell or during purification of the fusion proteins from the cell.

Preferably the antibody molecule is conjugated with the cytokine by means of a peptide bond, e.g. within a fusion protein comprising the TNFα or IL2 and the antibody molecule or a polypeptide chain thereof. See WO01/66298 and Borsi et al. [4] for further information on preparation of immunoconjugates comprising TNFα or IL2. See Carnemolla et al. [2], Taniguchi et al. [13], Maeda et al. [14] or Devos et al. [15] for further IL2 sequence information useful in preparation of a fusion polypeptide comprising IL2.

TNFα used in immunoconjugates of the invention is preferably human TNFα. IL2 is preferably human IL-2. Antibody molecules are preferably human or humanised antibody molecules.

Also described is a method comprising formulating the immunoconjugate into a pharmaceutical composition. Generally this involves purifying the immunoconjugate and combining it with a physiologically acceptable carrier.

Compositions according to the present invention, and for use in accordance with the present invention, may comprise, in addition to active ingredient (immunoconjugate), a pharmaceutically acceptable excipient, carrier, buffer, stabiliser or other materials well known to those skilled in the art. Such materials should be non-toxic and should not interfere with the efficacy of the active ingredient. For injection at the tumour site, the immunoconjugate may be in the form of a parenterally acceptable aqueous solution which is pyrogen-free and has suitable pH, isotonicity and stability.

BRIEF DESCRIPTION OF THE DRAWINGS

FIG. 3 shows the amino acid sequence of scFv(L19) (SEQ ID NO: 10). The VH and VL domains are shown separately (SEQ ID NO: 7 and SEQ ID NO: 9, respectively). The CDR1, 2 and 3 sequences in both the VH and VL domain are shown underlined. The VH and VL domains are separated by a 12 residue peptide linker sequence (SEQ ID NO: 8).

EXPERIMENTS

Example 1—Intratumoral Combination L19-IL2 and L19-muTNF

Figure 1A:
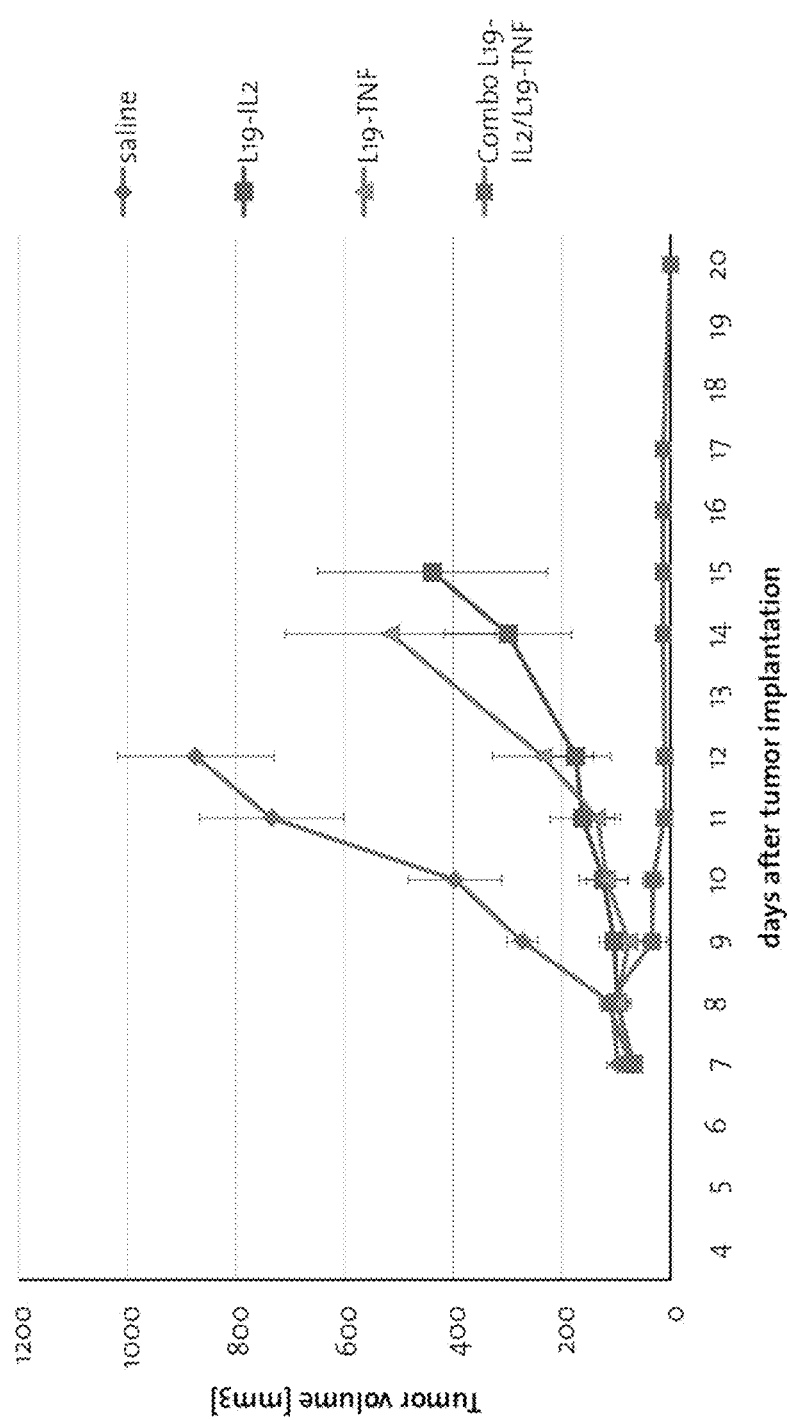
FIG. 1A shows tumour volume over time in the experiment described in Example 1.

Procedure
Mouse strain: female, immunocompetent 10 weeks old 129SVE mice
20 Million F9 cells were implanted
Treatment was started at day 7 after tumour implantation
On day 7, mice received a single intratumoural injection of 30 µg L19-IL2, 7 µg L19-muTNF, the combination or PBS. The total volume injected was 90 µl.
No further injections were given.
Tumour volume was measured daily.
Results
Tumour volume measured from day 7 to day 12 (FIG. 1A)—average results.
Tumours of mice who received only saline increased in size from about day 8 onwards.
Tumours of mice who received a single immunocytokine began to increase in size slowly from about day 10.
Tumours of mice who received the combination of immunocytokines decreased in size from day 9. By day 11 and 12, tumour volume was barely measurable. No tumour growth was observed in follow up measurements taken until day 20, when tumour volume was measured at zero. Weight of the mice was also recorded over time (FIG. 2).
Visual observations on day 10 after tumour implantation:
Large subcutaneous tumours had formed in the PBS-treated (control) mice (n=4 mice).
Visible tumours were present in the mice treated with L19-IL2 and L19-TNF, but markedly smaller than the tumours in control mice, and tumours were barely visible or not visible in the mice treated with the combination (n=5 mice in each group).

The results indicate that the single administration of the combination of immunocytokines was successful in achieving complete eradication of the treated tumour. It was observed that tumours did not regrow in the mice.

Further Details

When tumours reached a size of 70 mm$^3$ mice were randomly grouped and treatment was started. Mice received a single intratumoral injection of L19-IL2 (30 μg), L19-TNF (7 μg) or the combination in a volume of 90 μl PBS. The mice were monitored daily, and tumour volume was measured with a caliper, using the formula volume=length× width$^2$×0.5.

Figure 1B:
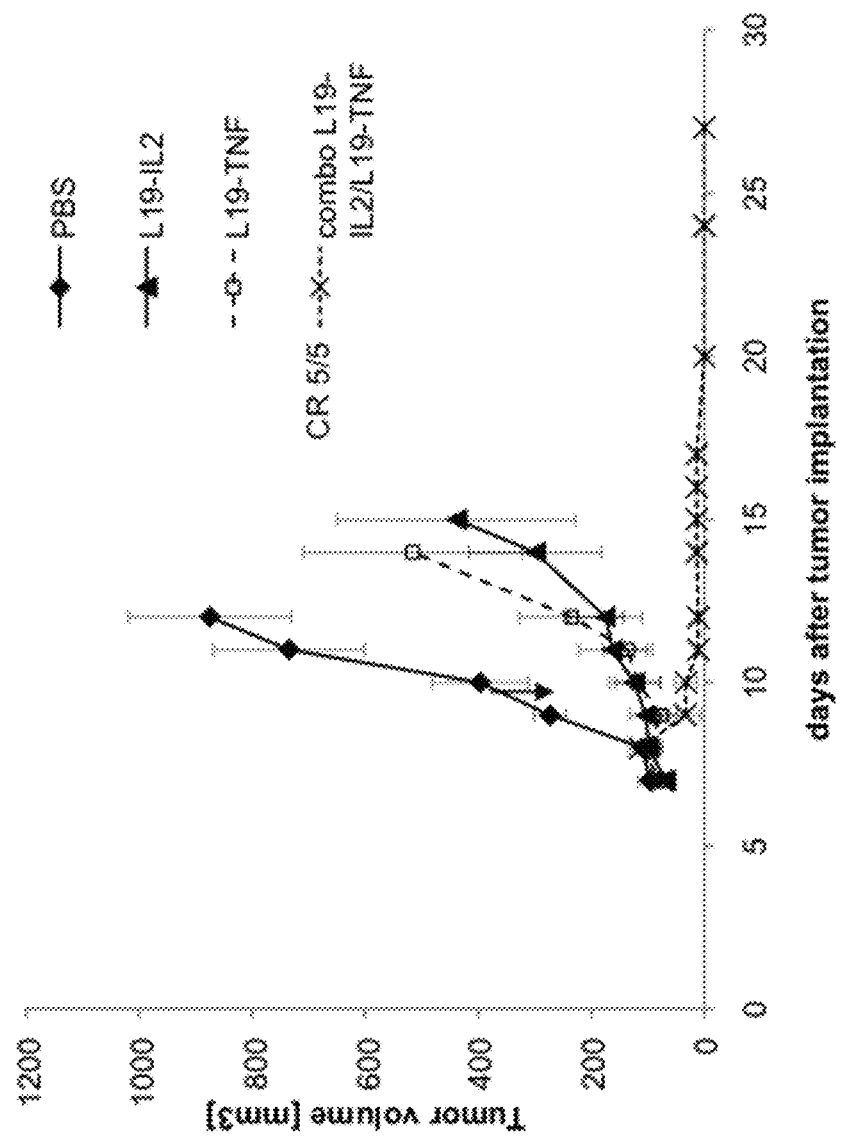
FIG. 1B shows follow up data supplementary to FIG. 1A.
Figure 2:
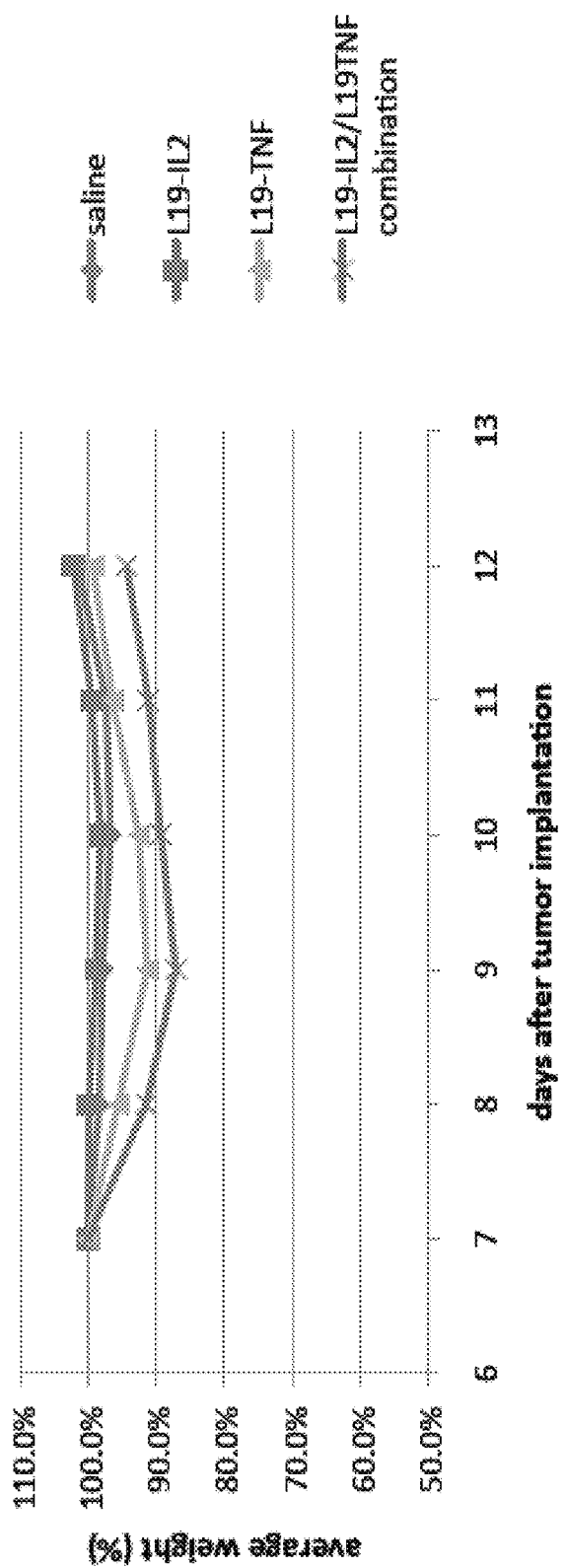
FIG. 2 shows average weight of the mice over time in the experiment described in Example 1.

FIG. 1B shows continuation of the data shown in FIG. 1A. The mice treated with the combination remained without any measurable tumour in further follow up measurements until day 27. Five out of five mice in this group achieved clinical response.

REFERENCES

1. Weide et al. *Cancer* 1 Sep. 2010:4139-4146
2. Carnemolla et al. *Blood* 99:1659-1665 2002
3. Christ et al. *Clin Cancer Res* 7(5):1385-97 2001
4. Borsi et al. *Blood* 102:4384-4392 2003
5. Kontermann, R & Dubel, S, *Antibody Engineering*, Springer-Verlag New York, LLC; 2001, ISBN: 3540413545
6. Mendez, M. et al. *Nature Genet,* 15(2): 146-156 1997
7. Knappik et al. J. Mol. Biol. (2000) 296, 57-86
8. Krebs et al. Journal of Immunological Methods 254 2001 67-84
9. Bird et al, Science, 242, 423-426, 1988
10. Huston et al, PNAS USA, 85, 5879-5883, 1988
11. Reiter, Y. et al, Nature Biotech, 14, 1239-1245, 1996
12. Holt et al *Trends in Biotechnology* 21, 484-490 2003
13. Taniguchi et al. *Nature* 302:305-310 1983
14. Maeda et al. *Biochem Biophys Res Comm* 115:1040-1047 1983
15. Devos et al. *Nucl Acids Res* 11:4307-4323 1983

What is claimed is:

1. A method of treating at least one skin tumor in a patient, comprising injecting an effective amount of a single dose of L19-tumor necrosis factor-α (L19-TNFα) immunoconjugate and a single dose of L19-interleukin-2 (L19-IL2) immunoconjugate at the tumor site, wherein the single dose of L19-TNFα immunoconjugate and the single dose of L19-IL2 immunoconjugate are administered together as a mixture, and wherein the method comprises treating at least one skin tumor by injecting a single administration of the mixture at the site of the tumor, wherein the mixture consists of L19-TNFα and L19-IL2 immunoconjugates in a parenterally acceptable aqueous solution, and optionally one or more pharmaceutically acceptable excipients.

2. A method according to claim 1, wherein each L19 part of the L19-TNFα immunoconjugate and the L19-IL2 immunoconjugate comprises the L19 complementary determining regions (CDRs), wherein the L19 CDRs are:

```
VH CDR1    SFSMS            SEQ ID NO: 1
VH CDR 2   SISGSSGTTYYADSVKG SEQ ID NO: 2
VH CDR 3   PFPYFDY          SEQ ID NO: 3
VL CDR 1   RASQSVSSSFLA     SEQ ID NO: 4
VL CDR 2   YASSRAT          SEQ ID NO: 5
VL CDR 3   QQTGRIPPT        SEQ ID NO: 6.
```

3. A method according to claim 2, wherein each L19 part of the L19-TNFα immunoconjugate and the L19-IL2 immunoconjugate further comprises the L19 VH domain SEQ ID NO: 7 and the L19 VL domain SEQ ID NO: 9.

4. A method according to claim 1, wherein the L19 part for each of the L19-TNFα immunoconjugate and the L19-IL2 immunoconjugate is scFv-L19 SEQ ID NO: 10.

5. A method according to claim 1, wherein one or both immunoconjugates carries a detectable label.

6. A method according to claim 1, wherein the injection is intratumoral injection.

7. A method according to claim 1, wherein the skin tumor is a primary tumor.

8. A method according to claim 1, wherein the skin tumor is melanoma.

9. A method according to claim 1, wherein the skin tumor is a carcinoma.

10. A method according to claim 1, wherein treating the tumor comprises eradicating the tumor.

11. The method of claim 10, wherein the tumor does not regrow.

12. The method of claim 1, wherein more than one tumor is treated.

13. The method of claim 1, wherein complete eradication of more than one tumor is achieved.

14. The method of claim 13, wherein the tumors do not regrow.

15. A method of treating at least one skin tumor in a patient, comprising injecting an effective amount of L19-tumor necrosis factor-α (L19-TNFα) immunoconjugate and L19-interleukin-2 (L19-IL2) immunoconjugate at the tumor site, wherein the L19-TNFα immunoconjugate and the L19-IL2 immunoconjugate are administered together as a mixture consisting of L19-TNFα and L19-IL2 in a parenterally acceptable aqueous solution, and optionally one or more pharmaceutically acceptable excipients, in a single dose, and wherein the skin tumor is a carcinoma or a melanoma.

16. The method of claim 15, wherein the skin tumor is a melanoma.

17. The method of claim 15, wherein additional dosages of the mixture of immunoconjugates are administered if the patient has a recurrence of the tumor, or if new tumors develop.

* * * * *